(12) United States Patent
Parsons et al.

(10) Patent No.: US 9,182,467 B2
(45) Date of Patent: Nov. 10, 2015

(54) COMPARATIVE ANALYSIS OF PROTEIN CONFORMATIONS BY USING 2D NOESY NMR SPECTRA

(75) Inventors: Ian Christopher Parsons, Belmont, MA (US); Jonathan Lansing, Reading, MA (US); Carlos J. Bosques, Arlington, MA (US); Daniela Beccati, Boston, MA (US)

(73) Assignee: Momenta Pharmaceuticals, Inc., Cambridge, MA (US)

(*) Notice: Subject to any disclaimer, the term of this patent is extended or adjusted under 35 U.S.C. 154(b) by 861 days.

(21) Appl. No.: 12/595,867

(22) PCT Filed: Apr. 15, 2008

(86) PCT No.: PCT/US2008/060331
§ 371 (c)(1),
(2), (4) Date: Mar. 8, 2010

(87) PCT Pub. No.: WO2008/128219
PCT Pub. Date: Oct. 23, 2008

(65) Prior Publication Data
US 2010/0188084 A1     Jul. 29, 2010

Related U.S. Application Data

(60) Provisional application No. 60/923,685, filed on Apr. 16, 2007.

(51) Int. Cl.
*G01N 24/08*     (2006.01)
*G01R 33/48*     (2006.01)
(Continued)

(52) U.S. Cl.
CPC .......... *G01R 33/4633* (2013.01); *G01N 24/087* (2013.01); *G01R 33/1269* (2013.01); *G01R 33/465* (2013.01); *G01N 24/08* (2013.01); *G01R 33/48* (2013.01); *G01R 33/5605* (2013.01)

(58) Field of Classification Search
CPC ..... G01N 24/087; G01N 24/08; G01N 24/00; G01R 33/1269; G01R 33/12; G01R 33/00; G01R 33/48; G01R 33/44; G01R 33/20; G01R 33/465; G01R 33/4633; G01R 33/5605; G01R 33/56; G01R 33/54
USPC ............................................... 506/7; 436/173
See application file for complete search history.

(56) References Cited

U.S. PATENT DOCUMENTS 5,122,469 A    6/1992    Mather et al.
5,633,162 A    5/1997    Keen et al.
(Continued)

FOREIGN PATENT DOCUMENTS

WO    WO-2008128219 A1    10/2008

OTHER PUBLICATIONS

Li, Hong et al., "NMR Studies of Thermal Denaturation and Cation-Mediated Aggregation of beta lactoglobulin," 1994, Journal of Agricultural Food Chemistry, 42, pp. 2411-2420.*
(Continued)

*Primary Examiner* — Christine T Mui
(74) *Attorney, Agent, or Firm* — Choate, Hall & Stewart LLP; Brenda H. Jarrell; Rolando Medina (57) ABSTRACT

The present disclosure provides a method for determining the relative conformations of a protein provided in different protein preparations, comprising steps of: (i) obtaining a first 2D NOESY NMR spectrum of a first protein preparation; (ii) obtaining a second 2D NOESY NMR spectrum of a second protein preparation; and (iii); determining whether a protein has a different conformation in the first and second protein preparations by comparing one or more cross-peaks in the first 2D NOESY NMR spectrum with one or more corresponding cross-peaks in the second 2D NOESY NMR spectrum.

34 Claims, 1 Drawing Sheet

(51) Int. Cl.
    *G01R 33/465*      (2006.01)
    *G01R 33/56*      (2006.01)
    *G01N 24/00*      (2006.01)
    *G01R 33/00*      (2006.01)
    *G01R 33/46*      (2006.01)
    *G01R 33/12*      (2006.01)

(56) References Cited

U.S. PATENT DOCUMENTS

| | | | |
|---|---|---|---|
| 6,075,134 | A | 6/2000 | Bertozzi et al. |
| 6,458,937 | B1 | 10/2002 | Bertozzi et al. |
| 2006/0084065 | A1 | 4/2006 | Tran |
| 2006/0127950 | A1 | 6/2006 | Bosques et al. |

OTHER PUBLICATIONS

Wimmer, Reinhard et al., "Towards a molecular level understanding of protein stabilization: the interaction between lysozyme and sorbitol," 1997, Journal of Biotechnology, 55, pp. 85-100.*
Redfield, Christina and Christopher M. Dobson, "Sequential 1H NMR Assignments and Secondary Structure of Hen Egg White Lysozyme in Solution," 1988, Biochemistry, 27, pp. 122-136.*
Wyss, Daniel F. et al., "Conformation and Function of the N-linked Glycan in the Adhesion Doman of Human CD2," Sep. 1, 1995, Science, 269, pp. 1273-1278.*
Belloque, Josefina et al., "Application of NMR spectroscopy to milk and dairy products," 1999, Trends in Food Science and Technology, 10, pp. 313-320.*
Vanhaverbeke, Cecile et al., "NMR characterization of the interaction between the C-terminal domain of interferon-gamma and heparin-derived oligosaccharides," 2004, Biochemical Journal, 384, pp. 93-99.*
Pascal, S. M. et al., "High-resolution structure and dynamic implications for a double-helical gramicidin A conformer," 1993, Journal of Biomolecular NMR, 3, pp. 495-513.*
McAlister, Mark S. B. et al 1998 Protein Engineering 11: 847-853.*
Kuhlmann, Martin et al 2006 Nephrol Dial Transplant 21 [Suppl 5]: v4-v8.*
Sibille, Nathalie et al 2002 J. Am. Chem. Soc 124: 14616-14625.*
Yuan et al 2000 Langmuir 16: 3030-3035.*
Vinogradova et al 2002 Cell 110: 587-597.*

International Search Report for PCT/US08/060331 (Apr. 15, 2008).
Koenig B W et al., 2002, "Structure and Orientation of a G Protein Fragment in the Receptor Bound State from Residual Dipolar Couplings," *J. Molecular Biology*, London, GB, 322:441-461.
Pervushin K V et al., 1992, "Three-Dimensional Structure of 1-36 Bacterioopsin in Methanol Chloroform Mixture and SDS Micelles Determined by 2D Proton NMR Spectroscopy," *Febs. Letters*, 308:190-196.
Picone et al., 2001, "Bacterial expression and confirmation al analysis of a chemosensory protein from Schistocerca gregaria," *Eur. J. Biochem.* 268:4794-4801.
Tessari Marco et al., 1997, "Heteronuclear NMR studies on the combined Src homology domains 2 and 3 of pp60 c-Src: Effects of phosphopeptide binding," *Biochemistry*, 36:14561-14571.
Written Opinion for PCT/US08/060331 (Apr. 15, 2008).
Dalpathado et al., "Comparative Glycomics fo the Glycoprotein Follicle Stimulating Hormone: Glycopeptide Analysis of Isolates from Two Mammalian Species" Biochemistry (2006), 45 (28), pp. 8665-8673.
Hitchcock et al., "Glycoform Quantification of Chondroitin/Dermatan Sulfate Using a Liquid Chromatography-Tandem Mass Spectrometry Platform" Biochemistry, (2006), 45(7), pp. 2350-2361.
Shimaoka et al., "One-pot solid-phase glycoblotting and probing by transoximization for high-throughput glycomics and glycoproteomics" ChemistryA European Journal, (2007), 13 (6), pp. 1664-1673.
Uematsu et al., "High throughput quantitative glycomics and glycoform-focused proteomics of murine dermis and epidermis" Molecular and Cellular Proteomics, (2005), 4 (12), pp. 1977-1989.
Xie et al., "Method for the Comparative Glycomic Analyses of O-Linked, Mucin-Type Oligosaccharides" Analytical Chemistry, (2004) vol. 76 (17), pp. 5186-5197.
Yuan et al., "Isotope tag method for quantative analysis of carbohydrates by liquid chromatography-mass spectrometry" Journal of Chromatography, (2005), 1067 (1-2), pp. 145-152.
Pace, et al., "Characterization of Minor N-linked Glycans on Antibodies Using Endo H Release and MALDI-Mass Spectrometry," Analytical Letters, 42: 1711-1724, 2009.
Anglister, et al., Interactions of Antibody Aromatic Residues with a Peptide of Cholera Toxin Observed by Two-Dimensional Transferred Nuclear Overhauser Effect Difference Spectroscopy, Biochemistry, 28:3360-3365 (1989).
Beck, Biosimilar, biobetter and next generation therapeutic antibodies, mAbs, 3:107-110 (2011).

* cited by examiner

COMPARATIVE ANALYSIS OF PROTEIN CONFORMATIONS BY USING 2D NOESY NMR SPECTRA

CROSS-REFERENCE TO RELATED APPLICATIONS

This application claims the benefit under 35 U.S.C. §371 of International Application Number PCT/US08/60331 (published on Oct. 23, 2008, as PCT publication number WO/2008/128219), filed Apr. 15, 2008 ("the '331 application"), which claims priority under 35 U.S.C. §119(e) to U.S. provisional application, Ser. No. 60/923,685, filed Apr. 16, 2007, the entire contents of each of which are incorporated herein by reference.

BACKGROUND

Protein therapeutic preparations include one or more species of proteins (e.g., differentially post-translationally modified species, different glycoforms, etc.) secreted from cell culture or isolated from a cell's surface as the biologically active ingredient. Alteration of the protein's conformation or aggregation state is known to affect its biological activity, immunogenicity, and biophysical properties. For example, a protein's conformation or aggregation state will affect its ability to interact with a target molecule (e.g., the protein therapeutic erythropoietin with the erythropoietin receptor) as well as its stability (e.g., its susceptibility to precipitation).

Since protein conformations may vary in response to changes in manufacturing conditions, qualitative and/or quantitative assessments of batch homogeneity is important during development and marketing of a protein therapeutic. Assessment of protein preparations during optimization of the manufacturing process is also important. The ability to make comparisons between protein preparations from different sources (e.g., generic vs. FDA approved originator) would also be useful.

There is therefore a need in the art for analytical techniques that can provide a detailed understanding of differences in protein conformation between different protein preparations.

SUMMARY

The present disclosure provides strategies for comparing protein preparations. In one aspect, the protein preparations are prepared by different methods. In particular, where the same protein is produced in different cells and/or under different conditions, and optionally is isolated under different conditions, the final protein preparations may not be identical. The present disclosure provides a system for tracking and comparing conformational differences in such different protein preparations.

A variety of techniques are known in the art for analyzing protein conformation including optical measurements such as circular dichroism (CD), differential scanning calorimetery (DSC), dynamic light scattering (DLS), fluorescence emission spectroscopy, derivative UV spectroscopy, or FTIR spectroscopy. These optical techniques provide an indirect and averaged measurement of protein conformation. As a result, they cannot detect the more subtle conformational differences that occur at the atomic level. The methods are based, in part, on the observation that a more detailed comparison between the conformations in protein preparations can be obtained by using NMR spectroscopy.

Thus, in one aspect, the present disclosure provides a method for determining the relative conformations of a protein provided in different protein preparations, comprising steps of: (i) obtaining a first 2D NOESY NMR spectrum of a first protein preparation; (ii) obtaining a second 2D NOESY NMR spectrum of a second protein preparation; and (iii); determining whether a protein has a different conformation in the first and second protein preparations by comparing one or more cross-peaks in the first 2D NOESY NMR spectrum with one or more corresponding cross-peaks in the second 2D NOESY NMR spectrum.

DEFINITIONS

Approximately, About: As used herein, the term "approximately" or "about," as applied to one or more values of interest, refers to a value that is similar to a stated reference value. In certain embodiments, the terms "approximately" or "about" refer to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less of the stated reference value.

Biological sample: The term "biological sample", as used herein, refers to any solid or fluid sample obtained from, excreted by or secreted by any living cell or organism, including, but not limited to, tissue culture, bioreactors, human or animal tissue, plants, fruits, vegetables, single-celled microorganisms (such as bacteria and yeasts) and multicellular organisms. For example, a biological sample can be a biological fluid obtained from, e.g., blood, plasma, serum, urine, bile, seminal fluid, cerebrospinal fluid, aqueous or vitreous humor, or any bodily secretion, a transudate, an exudate (e.g., fluid obtained from an abscess or any other site of infection or inflammation), or fluid obtained from a joint (e.g., a normal joint or a joint affected by disease such as a rheumatoid arthritis, osteoarthritis, gout or septic arthritis). A biological sample can also be, e.g., a sample obtained from any organ or tissue (including a biopsy or autopsy specimen), can comprise cells (whether primary cells or cultured cells), medium conditioned by any cell, tissue or organ, tissue culture.

Cell-surface protein: As used herein, the term "cell-surface protein" refers to a protein, at least a portion of which is present on the exterior surface of a cell. In some embodiments a "cell-surface protein" may be a cell-surface glycoprotein positioned on the cell-surface such that at least one of the glycan structures is present on the exterior surface of the cell.

Cell-surface glycan: A "cell-surface glycan" is a glycan that is present on the exterior surface of a cell. In many embodiments, a cell-surface glycan is covalently linked to a polypeptide as part of a cell-surface glycoprotein. A cell-surface glycan can also be linked to a cell membrane lipid.

Glycan: As is known in the art and used herein "glycans" are sugars. Glycans can be monomers or polymers of sugar residues, but typically contain at least three sugars, and can be linear or branched. A glycan may include natural sugar residues (e.g., glucose, N-acetylglucosamine, N-acetyl neuraminic acid, galactose, mannose, fucose, hexose, arabinose, ribose, xylose, etc.) and/or modified sugars (e.g., 2'-fluororibose, 2'-deoxyribose, phosphomannose, 6' sulfo N-acetylglucosamine, etc). The term "glycan" includes homo and heteropolymers of sugar residues. The term "glycan" also encompasses a glycan component of a glycoconjugate (e.g., of a glycoprotein, glycolipid, proteoglycan, etc.). The term also encompasses free glycans, including glycans that have been cleaved or otherwise released from a glycoconjugate.

Glycoconjugate: The term "glycoconjugate", as used herein, encompasses all molecules in which at least one sugar moiety is covalently linked to at least one other moiety. The term specifically encompasses all biomolecules with covalently attached sugar moieties, including for example N-linked glycoproteins, O-linked glycoproteins, proteoglycans, etc.

Glycoform: The term "glycoform", is used herein to refer to a particular form of a glycoconjugate. That is, when the same backbone moiety (e.g., polypeptide, lipid, etc) that is part of a glycoconjugate has the potential to be linked to different glycans or sets of glycans, then each different version of the glycoconjugate (i.e., where the backbone is linked to a particular set of glycans) is referred to as a "glycoform".

Glycoprotein: As used herein, the term "glycoprotein" refers to a protein that contains one or more covalently linked sugar moieties (i.e., glycans). The sugar moiety(ies) may be in the form of monosaccharides, disaccharides, oligosaccharides, and/or polysaccharides. The sugar moiety(ies) may comprise a single unbranched chain of sugar residues or may comprise one or more branched chains. In certain embodiments, sugar moieties may include sulfate and/or phosphate groups. Alternatively or additionally, sugar moieties may include acetyl, glycolyl, propyl or other alkyl modifications. In certain embodiments, glycoproteins contain O-linked sugar moieties; in certain embodiments, glycoproteins contain N-linked sugar moieties.

Glycoprotein: As used herein, the term "glycoprotein" refers to a protein that contains a peptide backbone covalently linked to one or more sugar moieties (i.e., glycans). As is understood by those skilled in the art, the peptide backbone typically comprises a linear chain of amino acid residues. In certain embodiments, the peptide backbone spans the cell membrane, such that it comprises a transmembrane portion and an extracellular portion. In certain embodiments, a peptide backbone of a glycoprotein that spans the cell membrane comprises an intracellular portion, a transmembrane portion, and an extracellular portion. In certain embodiments, methods comprise cleaving a cell surface glycoprotein with a protease to liberate the extracellular portion of the glycoprotein, or a portion thereof, wherein such exposure does not substantially rupture the cell membrane. The sugar moiety(ies) may be in the form of monosaccharides, disaccharides, oligosaccharides, and/or polysaccharides. The sugar moiety(ies) may comprise a single unbranched chain of sugar residues or may comprise one or more branched chains. In certain embodiments, sugar moieties may include sulfate and/or phosphate groups. Alternatively or additionally, sugar moieties may include acetyl, glycolyl, propyl or other alkyl modifications. In certain embodiments, glycoproteins contain O-linked sugar moieties; in certain embodiments, glycoproteins contain N-linked sugar moieties. In certain embodiments, methods disclosed herein comprise a step of analyzing any or all of cell surface glycoproteins, liberated fragments (e.g., glycopeptides) of cell surface glycoproteins, cell surface glycans attached to cell surface glycoproteins, peptide backbones of cell surface glycoproteins, fragments of such glycoproteins, glycans and/or peptide backbones, and combinations thereof.

Glycosylation pattern: As used herein, the term "glycosylation pattern" refers to the set of glycan structures present on a particular sample. For example, a particular glycoconjugate (e.g., glycoprotein) or set of glycoconjugates (e.g., set of glycoproteins) will have a glycosylation pattern. In some embodiments, reference is made to the glycosylation pattern of cell-surface glycans. A glycosylation pattern can be characterized by, for example, the identities of glycans, amounts (absolute or relative) of individual glycans or glycans of particular types, degree of occupancy of glycosylation sites, etc., or combinations of such parameters.

Glycoprotein preparation: A "glycoprotein preparation", as that term is used herein, refers to a set of individual glycoprotein molecules, each of which comprises a polypeptide having a particular amino acid sequence (which amino acid sequence includes at least one glycosylation site) and at least one glycan covalently attached to the at least one glycosylation site. Individual molecules of a particular glycoprotein within a glycoprotein preparation typically have identical amino acid sequences but may differ in the occupancy of the at least one glycosylation sites and/or in the identity of the glycans linked to the at least one glycosylation sites. That is, a glycoprotein preparation may contain only a single glycoform of a particular glycoprotein, but more typically contains a plurality of glycoforms. Different preparations of the same glycoprotein may differ in the identity of glycoforms present (e.g., a glycoform that is present in one preparation may be absent from another) and/or in the relative amounts of different glycoforms.

N-glycan: The term "N-glycan", as used herein, refers to a polymer of sugars that has been released from a glyconjugate but was formerly linked to the glycoconjugate via a nitrogen linkage (see definition of N-linked glycan below).

N-linked glycans: N-linked glycans are glycans that are linked to a glycoconjugate via a nitrogen linkage. A diverse assortment of N-linked glycans exists, but is typically based on the common core pentasaccharide $(Man)_3(GlcNAc)(GlcNAc)$.

O-glycan: The term "O-glycan", as used herein, refers to a polymer of sugars that has been released from a glycoconjugate but was formerly linked to the glycoconjugate via an oxygen linkage (see definition of O-linked glycan below).

O-linked glycans: O-linked glycans are glycans that are linked to a glycoconjugate via an oxygen linkage. O-linked glycans are typically attached to glycoproteins via N-acetyl-D-galactosamine (GalNAc) or via N-acetyl-D-glucosamine (GlcNAc) to the hydroxyl group of L-serine (Ser) or L-threonine (Thr). Some O-linked glycans also have modifications such as acetylation and sulfation. In some instances O-linked glycans are attached to glycoproteins via fucose or mannose to the hydroxyl group of L-serine (Ser) or L-threonine (Thr).

Protease: The term "protease" as used herein refers to an agent that cleaves a peptide bond between sequential amino acids in a polypeptide chain. In some embodiments, a protease is an enzyme (i.e., a proteolytic enzyme). In certain embodiments, a protease is a protein (e.g., a protein enzyme) comprising one or more polypeptide chains. In certain embodiments, a protease is a chemical cleavage agent.

Protein: In general, a "protein" is a polypeptide (i.e., a string of at least two amino acids linked to one another by peptide bonds). Proteins may include moieties other than amino acids (e.g., may be glycoproteins) and/or may be otherwise processed or modified. Those of ordinary skill in the art will appreciate that a "protein" can be a complete polypeptide chain as produced by a cell (with or without a signal sequence), or can be a functional portion thereof. Those of ordinary skill will further appreciate that a protein can sometimes include more than one polypeptide chain, for example linked by one or more disulfide bonds or associated by other means.

Protein preparation: The term "protein preparation" as used herein refers to a mixture of proteins obtained according to a particular production method. The proteins in a protein preparation may be the same or different, i.e., a protein preparation may include several copies of the same protein and/or a mixture of different proteins. The production method will generally include a recombinant preparation step using cultured cells that have been engineered to express the proteins in the protein preparation (or to express the proteins at a relevant level or under relevant conditions). The production method may further include an isolation step in which proteins are isolated from certain components of the engineered cells (e.g., by lyzing the cells and pelleting the protein component by centrifugation). The production method may also include a purification step in which the proteins in the protein preparation are separated (e.g., by chromatography) from other cellular components, e.g., other proteins or organic components that were used in earlier steps. It will be appreciated that these steps are non-limiting and that any number of additional productions steps may be included. Different protein preparations may be prepared by the same production method but on different occasions (e.g., different batches). Alternatively, different protein preparations may be prepared by different production methods. Two production methods may differ in any way (e.g., expression vector, engineered cell type, culture conditions, isolation procedure, purification conditions, etc.).

Signal intensity: As used herein, the terms "signal intensity" refer to the magnitude of a particular signal (e.g., a NOESY cross-peak) within an NMR spectrum. The terms "signal intensity" and "cross-peak intensity" are used interchangeably. In one embodiment, the signal intensity is obtained by measuring the signal area or volume. In one embodiment, the signal intensity is obtained by measuring the signal height.

Substantially: As used herein, the term "substantially" refers to the qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. The term "substantially" is therefore used herein to capture the potential lack of completeness inherent in many biological and chemical phenomena. To give but one particular example, when it is said that a treatment does not "substantially" rupture the cell membranes, it is meant to indicate that all or most of the cell membranes remain intact during and after the treatment, for example so that intracellular glycoproteins are thus not released from the cells. In certain embodiments, the term "substantially", as applied to unruptured cell membranes, refers to condition wherein 15%, 10%, 9%, 8%, 7%, 6%, 5%, 4%, 3%, 2%, 1%, or fewer of the cells subjected to a particular treatment exhibit measurable ruptured cell membranes. In certain embodiments, the term "substantially", as applied to unruptured cell membranes, refers to condition wherein none of the cells subjected to a particular treatment exhibit measurable ruptured cell membranes.

DETAILED DESCRIPTION OF CERTAIN EMBODIMENTS

As indicated, the present disclosure provides strategies for comparing different protein preparations. In many embodiments, the strategies are employed to compare different preparations of the same protein (i.e., the same amino acid sequence), where the protein conformation may differ due to differences in preparation.

Thus, in one aspect, the present disclosure provides a method for determining the relative conformations of a protein provided in different protein preparations, comprising steps of: (i) obtaining a first 2D NOESY NMR spectrum of a first protein preparation; (ii) obtaining a second 2D NOESY NMR spectrum of a second protein preparation; and (iii); determining whether a protein has a different conformation in the first and second protein preparations by comparing one or more cross-peaks in the first 2D NOESY NMR spectrum with one or more corresponding cross-peaks in the second 2D NOESY NMR spectrum. In certain embodiments, the step of comparing may involve comparing the chemical shifts of the corresponding cross-peaks. Differences in chemical shift in either dimension may indicate a difference in protein conformation. In certain embodiments, the step of comparing may alternatively (or additionally) involve comparing the intensity of a cross-peak.

In certain embodiments, the second protein preparation is an appropriate standard. For example, the standard could be a commercially available protein preparation, e.g., a therapeutic protein product.

In certain embodiments, a table of NOESY signal intensities may be generated, and compared to a reference table of corresponding NOESY signal intensities. The reference table may be generated from an appropriate protein standard. Alternatively, the reference table may be generated from some statistical combination of protein standards or prior batches of the same protein. For example, the reference table may list averages, ranges, standard deviations, etc. for different NOESY signal intensities. By tabulating variations of signal intensities across multiple batches of a specific protein one can generate information regarding the extent to which different signal intensities vary across different lots and batches of a particular protein. This can be useful in identifying the NOESY cross-peaks that provide the most sensitive feedback on protein conformation.

In some embodiments, multiple batches of product A (e.g., a generic therapeutic protein) will be compared in this manner with multiple batches of product B (e.g., an originator therapeutic protein), in order to demonstrate the extent of variations between products A and B, and to thereby demonstrate conformational sameness between products A and B.

In some embodiments, one or more NOESY signals will be assigned to a particular atom-atom interaction within the protein. According to such embodiments, differences in these assigned NOESY peak volumes may be correlated with differences in the three-dimensional folding or aggregation states of batches of the protein.

2D NOESY NMR Spectra

According to the present disclosure, 2D NOESY NMR spectra of at least two protein preparations are obtained. 2D NOESY NMR is a well established NMR technique that generates correlations (cross-peaks in a 2D spectrum) between nuclei that are in close spatial proximity (e.g., see *Principles of Nuclear Magnetic Resonance in One or Two Dimensions*, by Ernst et al., Oxford University Press, 1992; *Protein NMR Spectroscopy: Principles and Practice* by Cavanagh et al., Academic Press, 2006 and *Protein NMR Techniques (Methods in Molecular Biology)* Ed. by Downing, Humana Press, 2004 and references cited therein). For example, in one embodiment, the technique can be used to generate correlations between neighbouring protons. This is to be contrasted with most other 2D NMR techniques (e.g., HSQC, TOCSY, etc.) that generate correlations between nuclei that are directly or indirectly linked by chemical bonds.

The NOESY technique relies on the Nuclear Overhauser Effect (NOE) which results from dipolar interactions between neighbouring nuclear spins. The intensity of the NOE is approximately proportional to $1/r^6$, with r being the distance between the nuclear spins. The correlation between two nuclei therefore depends on the distance between them. Typically NOE signals between neighbouring nuclei are only observed if they are separated by less than about 5 Å. The 2D NOESY NMR experiment therefore correlates all nuclei that are separated by less than about 5 Å. In the case of proteins, the nuclei may be at opposite ends of the primary amino acid sequence but brought into close proximity as a result of the protein's conformation. As a result, NOESY is a very powerful and detailed tool for studying the conformations of proteins.

In one embodiment, the methods involve obtaining 2D $^1$H-$^1$H NMR NOESY spectra of two or more protein preparations. Since protons (i.e., $^1$H) are naturally abundant (as opposed to non-zero spin heteronuclei such as $^{13}$C and $^{15}$N) 2D $^1$H-$^1$H NMR NOESY spectra can be readily obtained without the need for isotopically-enriched protein preparations. The 2D $^1$H-$^1$H NMR NOESY spectra may be obtained using any NMR spectrometer. High-field NMR spectrometers (e.g., greater than 600 MHz) are generally preferred over low-field NMR spectrometers since they produce higher resolution spectra and equivalent signal:noise ratios in shorter time periods. Similarly, it will be appreciated that the methods described herein are not limited to any specific pulse sequence or set of acquisition parameters (e.g., mixing time, acquisition time, etc.). In particular, it should be appreciated that the methods described herein are not restricted to specific variations of the NOESY pulse sequence, and for example, should also be considered to include the use of ROESY (Rotating frame Overhauser Experiment) pulse sequences. Pulse sequences and acquisition parameters will generally be optimized by the user depending on the nature of the NMR spectrometer and the protein preparation (e.g., concentration, molecular weight, spectral region of interest, etc).

Once the 2D NOESY NMR spectra have been obtained, the methods include a step of comparing one or more cross-peaks in the first 2D NOESY NMR spectrum with one or more corresponding cross-peaks in the second 2D NOESY NMR spectrum. As indicated above, the cross-peaks in a 2D NOESY NMR spectrum correspond to NOE signals between neighbouring nuclei (e.g., two neighbouring protons). In certain embodiments, the step of comparing may involve comparing the chemical shifts of the cross-peaks. Differences in chemical shift in either dimension may indicate a difference in protein conformation. In certain embodiments, the step of comparing may alternatively (or additionally) involve comparing the intensity of a cross-peak. A decrease (increase) in the intensity of a cross-peak will be indicative of an increase (decrease) in inter-nuclear separation. Differences in cross-peak intensity between two or more protein preparations can therefore be used as indicators of conformational variations.

In one embodiment, multiple cross-peaks in the two or more 2D NOESY NMR spectra are compared in order to provide a more detailed picture of conformational differences between the protein preparations. It will be appreciated that a simple algorithm could be used to identify corresponding cross-peaks in the two or more 2D NOESY NMR spectra based on chemical shift information. The algorithm could be set to allow for slight variations in chemical shift in order to pick up corresponding cross-peaks that may occur at slightly different shifts. The same algorithm could also be used to measure the cross-peak chemical shifts and intensities. An algorithm could then quantify any differences between the two or more 2D NOESY NMR spectra. The output could be in a variety of forms. In one embodiment, the algorithm could produce individual results for each common cross-peak. As discussed, these could be tabulated in some form. Alternatively (or additionally) the algorithm could combine some or all of the results for different cross-peaks, e.g., by producing a range, a mean, a median, a standard deviation, or any other suitable statistical metric.

When comparing several different protein preparations of the same protein over time it may prove advantageous to store the results (e.g., cross-peak chemical shifts and volumes or intensities) for each protein preparation in a library so that new results can be compared against individual entries within the library or statistical aggregates thereof (e.g., of entries that were obtained under the same set of experimental conditions). Over time, a set of results that correspond to some combination of individual library entries could be used as a "standard" to be compared against the 2D NMR NOESY spectra of new protein preparations.

Figure 1:
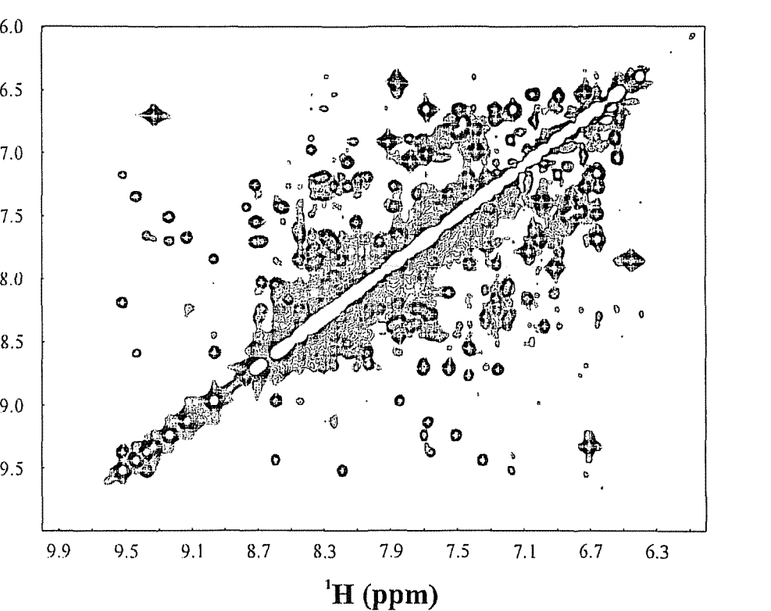
FIG. 1 shows the NH—NH correlation region of a 2D $^1$H-$^1$H NOESY NMR spectrum obtained for the protein CSP-sg4 (Picone et al., Eur. J. Biochem. 268:4794-4801, 2001). The spectrum was obtained at 1.2 mM protein concentration, in 50 mM sodium phosphate buffer, pH 6.8, at 300 K, with a 100 ms mixing time.

In general, it will be advantageous to compare cross-peaks that are (a) in uncrowded regions of the 2D NMR NOESY spectra and (b) result from inter-residue correlations. In general, cross-peaks in the amide NH—NH correlation region of a 2D NMR NOESY spectrum satisfy both of these conditions. Indeed, as shown in FIG. 1, the amide NH—NH correlation region (about 6 to 10 ppm) is well resolved since the amide NH chemical shift is highly sensitive to chemical environment and therefore well distributed in both dimensions. In addition, this region is well separated from the strong H$_2$O resonance (~4.8 ppm). Further, since each amino acid includes a single backbone amide, the correlations in this region are dominated by inter-residue correlations. Accordingly, in certain embodiments, the comparison step involves comparison of one or more cross-peaks in the amide NH—NH correlation region of the two or more 2D NMR NOESY spectra.

It is to be understood that cross-peaks in other regions may be used instead of (or in combination with) cross-peaks in this region. For example, in certain embodiments, the conformation step may involve correlations between amide NH nuclei and CH$_3$ methyl nuclei. In certain embodiments, the conformation step may involve correlations between CH$_3$ methyl nuclei. In some embodiments, the conformation step may involve correlations between amide NH nuclei and indole NH nuclei. In some embodiments, the conformation step may involve correlations between CH$_3$ methyl nuclei and indole NH nuclei. In some embodiments, the conformation step may involve correlations between amide NH nuclei and H-α nuclei. In some embodiments, the conformation step may involve correlations between amide NH nuclei and glycosidic nuclei (i.e., $^1$H nuclei from glycans present, e.g., in a glycoprotein). It is to be understood that this list is non-limiting and that any well resolved inter-residue NOESY cross-peak may be used according to the methods described herein.

In general, it is to be understood that the comparison step can be performed without assigning the cross-peaks to specific nuclei within the protein(s) in question. Indeed, the methods described herein take advantage of the fact that differences in cross-peak intensity and/or chemical shift are powerful indicators of conformational differences irrespective of the exact location of the reporting nuclei. In certain embodiments it may prove advantageous to assign one or more cross-peaks. If the NMR structure of the protein(s) in question has already been published then this may simply involve reviewing the relevant literature. If the NMR structure is unknown then a variety of methods are known in the art that may be used in order to assign specific cross-peaks to specific nuclei within the protein. Having assigned one or more cross-peaks one may advantageously select cross-peaks that are known to be associated with particular regions of the protein(s). For example, it may be known that a particular region of the protein(s) is particularly susceptible to conformational change. By selecting cross-peaks that correspond to this region one may be able to more closely monitor conformational variations across different protein preparations.

Protein Preparations

In one aspect, the methods of the present disclosure provide tools for comparing protein preparations obtained from different sources. The methods are not limited to any specific source or type of protein preparation. Thus, the methods can be applied to protein preparations obtained from a wide variety of sources including, but not limited to, therapeutic formulations and biological samples. A biological sample may undergo one or more analysis and/or purification steps prior to or after being analyzed. To give but a few examples, in some embodiments, a biological sample is treated with one or more proteases (e.g., to release cell-surface proteins); in some embodiments, proteins in a biological sample are labeled with one or more detectable markers or other agents that may facilitate analysis by NMR. Any of a variety of separation and/or isolation steps may be applied to a biological sample.

In one embodiment, the protein preparations may be obtained from cell cultures. Methods of providing a protein preparation from a cell, are described below and herein. Different protein preparations may be obtained by using, for example, different expression vectors; different cell types to generate the protein preparation; by varying cell culture conditions; or by obtaining different protein samples of the same cell culture at different time increments. As well, different protein preparations are provided upon varying any one of a number of cleavage, isolation, and/or purification conditions. These and other condition variables are also described below and herein.

In certain embodiments, the first protein preparation is isolated from a cell. In certain embodiments, the first protein preparation is isolated from a cell's surface. In certain embodiments, the first protein preparation is isolated from a cell's secretion. In certain embodiments, the first protein preparation is isolated from a lyzed cell. In certain embodiments, the first protein preparation includes a glycoprotein.

In certain embodiments, the second protein preparation is isolated from a cell. In certain embodiments, the second protein preparation is isolated from a cell's surface. In certain embodiments, the second protein preparation is isolated from a cell's secretion. In certain embodiments, the second protein preparation is isolated from a lysed cell. In certain embodiments, the second protein preparation includes a glycoprotein.

In certain embodiments, the first and second protein preparations are obtained from the same cell. In certain embodiments, the first and second protein preparations are obtained from different cells.

In certain embodiments, the first and second protein preparations are obtained using the same cell culture conditions. In certain embodiments, the first and second protein preparations are obtained using different cell culture conditions.

In certain embodiments, the first and second protein preparations are obtained from the same cell culture at different time increments. In certain embodiments, the first and second protein preparations are obtained from different cell cultures at the same time increments.

In certain embodiments, the first and second protein preparations are obtained using the same cleavage conditions (e.g., using the same protease to cleave a cell-surface protein from two difference cell cultures). In certain embodiments, the first and second protein preparations are obtained using different cleavage conditions (e.g., using the same protease but a different buffer to cleave a cell-surface protein from two difference cell cultures).

In certain embodiments, the first and second protein preparations are obtained using the same isolation conditions. In certain embodiments, the first and second protein preparations are obtained using different isolation conditions.

In certain embodiments, the first and second protein preparations are obtained using the same purification conditions. In certain embodiments, the first and second protein preparations are obtained using different purification conditions.

Recombinant Expression of Proteins and Growth of Cells in Cell Culture

Any of a variety of cells and/or cell lines capable of protein expression, including for example expression of a therapeutic protein, can be used to prepare a protein preparation. Suitable cells include, but are not limited to, mammalian cells, avian cells, fish cells, insect cells, plant cells, fungal cells, bacterial cells, and hybrid cells. In some embodiments, the cells have been engineered (e.g., genetically and/or chemically) to have one or more glycosylation characteristics more similar to human cells.

Exemplary mammalian cell lines that can be used include, but are not limited to, Chinese hamster ovary (CHO) cells, HeLa cells, Madin-Darby canine kidney (MDCK) cells, baby hamster kidney (BHK cells), NS0 cells, MCF-7 cells, MDA-MB-438 cells, U87 cells, A172 cells, HL60 cells, A549 cells, SP10 cells, DOX cells, DG44 cells, HEK 293 cells, SHSY5Y, Jurkat cells, BCP-1 cells, COS cells, Vero cells, GH3 cells, 9L cells, 3T3 cells, MC3T3 cells, C3H-10T1/2 cells, NIH-3T3 cells, and C6/36 cells.

Exemplary fish cell lines that can be used include, but are not limited to, ZF4 cells, AB9 cells, GAKS cells, OLF-136 cells, CAEP cells, CAF cells, OLHE-131 cells, OLME-104 cells, ULF-23 cells, BRF41 cells, Hepa-E1 cells, Hepa-T1 cells, GEM-81 cells, GEM-199 cells, GEM-218 cells, GAKS cells, D-11 cells, R1 cells, RTG-2 cells, RTO cells, and TPS cells. A more complete list can be found in Fryer and Lannan, 2005, "Three decades of fish cell culture: a current listing of cell lines derived from fishes," *J. Tissue Culture Methods*, 16:87-94.

Exemplary insect cell lines that can be used include, but are not limited to, SFM cells, Sf21 cells, Sf9 cells, Schneider cells, S2 cells, T.ni cells, SES-MaBr-1 cells, SES-MaBr-3 cells, NIAS-MB-25 cells, NIAS-MaBr-92 cells, FRI-SpIm-1229 cells, SES-MaBr-4 cells, NIAS-LeSe-11 cells, TUAT-SpLi-221 cells, NIAS-PX-64 cells, NIAS-MB-32 cells, NIAS-MaBr-93 cells, SES-MaBr-5 cells, BM-N cells, NIAS-PX-58 cells, MBHL-2 cells, and MBHL-3 cells.

Those of ordinary skill in the art will recognize that this is an exemplary, not a comprehensive, listing of various cell lines that may be used. Other cell lines may be advantageously utilized to produce a protein preparation.

In addition, those skilled in the art will appreciate that a variety of expression systems and vectors may be used in order to express a protein of interest within each of these cell lines (e.g., see *Molecular cloning: A Laboratory Manual*, Ed. by Sambrook, CSHL Press, 2002). Different expression systems may be used to prepare the first and second protein preparations.

Any of a variety of cell culture media, including complex media and/or serum-free culture media, that are capable of supporting growth of the one or more cell types or cell lines may be used. Typically, a cell culture medium contains a buffer, salts, energy source, amino acids (e.g., natural amino acids, non-natural amino acids, etc.), vitamins and/or trace elements. Cell culture media may optionally contain a variety of other ingredients, including but not limited to, carbon sources (e.g., natural sugars, non-natural sugars, etc.), cofactors, lipids, sugars, nucleosides, animal-derived components, hydrolysates, hormones/growth factors, surfactants, indicators, minerals, activators/inhibitors of specific enzymes, and organics (e.g., butyrate, which induces apoptosis, which releases glycosylases, often slows down growth rate of cell, which changes glycosyltransferase levels, which can result in more mature glycosylation; and results in change in energy of cell; chloroquin, which affects intracellular pH; betaine, an osmoprotectant; ammonia, which alters intracellular pH levels and which can change glycosyl transferase efficiency; etc.), and/or small molecule metabolites (e.g., CMP-sialic acid, glucosamine, Bertozzi compounds, e.g., see U.S. Pat. Nos. 6,075,134 or 6,458,937, etc.). Cell culture media suitable for use are commercially available from a variety of sources, e.g., ATCC (Manassas, Va.).

In certain embodiments, one or more of the following media are used to grow cells: RPMI-1640 Medium, Dulbecco's Modified Eagle's Medium, Minimum Essential Medium Eagle, F-12K Medium, Iscove's Modified Dulbecco's Medium. As will be understood by those of ordinary skill in the art, when defined medium that is serum-free and/or peptone-free is used, the medium is typically highly enriched for amino acids and trace elements (see, for example, U.S. Pat. No. 5,122,469 to Mather et al., and U.S. Pat. No. 5,633,162 to Keen et al.). Different cell culture media may affect the glycosylation pattern of glycoproteins expressed in that medium. For example, a given cell culture media may result in production of glycoproteins with an increased glycosylation pattern, a decreased glycosylation pattern, or a combination of increased and decreased glycosylation patterns. One of ordinary skill in the art will be aware of and will be able to choose one or more suitable cell culture media for use in growing cells whose proteins are to be analyzed.

In some embodiments, cells are cultured in batch culture, fed batch culture, perfusion culture, static suspension (e.g., roller bottles, T flasks, microcarriers, T150, etc.), and/or on shakers.

Cells used to generate a protein preparation can be grown under any of a variety of cell culture conditions. In some embodiments, cells are cultured under cell culture conditions such that a given protein in a protein preparation exhibits a desired glycosylation pattern. In some embodiments, one or more cell culture conditions are controlled and/or modified in order to produce proteins that exhibit more desirable glycosylation patterns. Such cell culture conditions include, but are not limited to, pH, $CO_2$ levels, oxygen levels, culture agitation rate, redox conditions, culture temperature, cell density, density of seed culture, duration of culture, reactor design, sparge rate, and/or osmolarity. One of ordinary skill in the art will be aware of and will be able to control and/or modify one or more cell culture conditions in order to produce proteins that exhibit more desirable glycosylation patterns.

Any of a variety of methods can be used to purify cells from the cell culture medium. In certain embodiments, cells are grown in a suspension culture. In such embodiments, cells may be purified from the cell culture medium by one or more cycles of centrifugation and washing (e.g., with a physiological suitable washing solutions such as phosphate-buffered saline). Care should be taken not to centrifuge the cells with too much force in order to avoid unnecessary cell breakage.

In certain embodiments, cells are grown in an adhesion culture. In such embodiments, cells may be purified from the cell culture medium by first releasing them from the culture surface. For example, cells may be released from the culture surface by subjecting them to EDTA. Those of ordinary skill in the art will be aware of other suitable agents that can be used to release adherent cells from the culture surface. After release, cells may be purified by one or more cycles of centrifugation and washing (e.g., with a physiological suitable washing solutions such as phosphate-buffered saline). As with cells grown in suspension culture, care should be taken not to centrifuge the cells with too much force in order to avoid unnecessary cell breakage.

Isolation of Proteins

Once the protein or proteins have been expressed within a cell culture the protein(s) can be isolated using any known isolation method.

In certain embodiments, the protein(s) may be secreted by the cell. According to such embodiments, the protein(s) can be directly isolated from the cell supernatant, e.g., by filtration or settling.

In certain embodiments, the protein(s) may remain within the outer membrane of the cell (e.g., in the cytoplasm or periplasm). According to such embodiments, the cellular structure may need to be disrupted in order to isolate the proteins. In one embodiment this is achieved by lyzing the cells (e.g., by sonication, using detergents, etc.) and then pelleting the protein component from the resulting lysate by centrifugation. The proteins within the pellet can then be separated by chromatography as is known in the art.

In certain embodiments, the protein(s) are cell-surface proteins (e.g., glycoproteins). According to such embodiments, the protein(s) can be liberated from the cell-surface by subjecting the cell to one or more proteases. This approach is more selective than cell lysis and avoids mixing the protein(s) of interest with undesired intracellular proteins, e.g, from the cytoplasm, the endoplasmic reticulum and/or Golgi apparatus. Proteases are enzymes that catalyze the hydrolysis of amide bonds within a polypeptide chain. Several classes of proteases exist including serine proteases, threonine proteases, cysteine proteases aspartic acid proteases, metalloproteases, and glutamic acid proteases. Non-limiting examples of proteases that can be used include trypsin, chymotrypsin, elastase, subtilisin, proteinase K, pepsin, ficin, bromelin, plasmepsin, renin, chymosin, papain, a cathepsin (e.g. cathepsin K), a caspase (e.g. CASP3, CASP6, CASP7, CASP14), calpain 1, calpain 2, hermolysin, carboxypeptidase A or B, matrix metalloproteinase, a glutamic acid protease, and/or combinations thereof. Those of ordinary skill in the art will be aware of a number of other proteases that can be used to release a protein from the surface of a cell.

In certain embodiments, proteins are liberated from the cell-surface by subjecting the cell to one or more proteases for a limited period of time in order to prevent substantial lysis of the cell membrane. In certain embodiments, a cell is subjected to one or more proteases for a sufficiently limited time such that substantial lysis of the cell membrane does not occur. For example, a cell may be subjected to one or more proteases for a period of time that is less than about 15, 14, 13, 12, 11, 10, 9, 8, 7, 6, 5, 4, 3, 2, or 1 minute. In certain embodiments, a cell is subjected to one or more proteases for a period of time that is more than 15 minutes so long as substantial lysis of the cell membrane does not occur. For example, a sufficiently low concentration of protease(s), a sufficiently low temperature and/or any of a variety of other factors or conditions may be employed such that the overall protease activity is decreased to a point where substantial lysis of the cell membrane does not occur. Those of ordinary skill in the art will be aware of and will be able to employ factors or conditions that ensure that substantial lysis of the cell membrane does not occur.

In certain embodiments, cell-surface proteins are liberated by subjecting a cell to one or more proteolytic enzymes at a concentration of at least about 0.1 mg/mL. In certain embodiments, cell-surface proteins are liberated by subjecting a cell to one or more proteolytic enzymes at a concentration of less than about 2.0 mg/mL. In certain embodiments, cell-surface proteins are liberated by subjecting a cell to one or more proteolytic enzymes at a concentration of about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.5, 3.0, 3.5, 4.0, 5.0, 6.0, 7.0, 8.0, 9.0, 10.0 mg/mL or higher.

In certain embodiments, cell-surface proteins are liberated by subjecting a cell to a plurality of proteases. For example, a cell may be subjected to 2, 3, 4, 5, 6, 7, 8, 9, 10, or more proteases to liberate cell-surface proteins. Such a plurality of proteases may be administered to the cell simultaneously and/or sequentially. In certain embodiments, cell-surface proteins are liberated by subjecting a cell to a plurality of proteases simultaneously, after which the liberated proteins are purified away from the cell.

In certain embodiments, cell-surface proteins are liberated by subjecting a cell to a first protease (or plurality of first proteases) for a first period of time, after which the cell is subjected to a second protease (or plurality of second proteases) for a second period of time. Prior to treatment with the second protease, the first protease may optionally be removed and/or inactivated. By way of example, the first protease may be inactivated incubating the protease at a temperature for a time sufficient to inactivate it. Additionally or alternatively, the first protease may be inactivated by incubating it with an inhibitor that is specific to the protease (e.g. an antibody or other molecule that specifically binds the first protease and inhibits its catalytic activity). Other methods of inactivating the first protease will be known to those of ordinary skill in the art. In the case where the first protease is inactivated by incubating it with a specific inhibitor, it will be appreciated that the presence of the inhibitor should not substantially inhibit the activity of the second protease.

Purification of Proteins

Once the protein or proteins have been isolated from the cell culture they may be further purified prior to NMR analysis. For example, other proteins and organic components that remain may be removed prior to analysis. This will be generally be achieved using a procedure that minimizes perturbations to the protein's conformation or aggregation state. In one embodiment, the protein will be dialyzed against a suitable buffer and then concentrated to a suitable concentration, in such a way that minimal perturbations to the existing conformation occur, and that repeated iterations of the procedure on separate aliquots of the protein, result in the same protein concentration and the same conformation, as revealed by 2D NOESY NMR.

In certain embodiments, the purification step may have the effect of concentrating the protein preparation to a level at which a 2D NOESY NMR spectrum can be obtained in a reasonable time. Thus, in one embodiment the protein preparation that is analyzed by NMR may have a final protein concentration of about 50 to 200 uM, e.g., about 75 to 125 uM.

Applications

It will be appreciated that the techniques described herein may be used in a variety of applications. In general, any application that requires the comparison of different protein preparations (e.g., preparations from different sources) may benefit from these methods.

Methods of the present disclosure may be used in one or more stages of process development for the production of a therapeutic or other commercially relevant protein of interest (including glycoproteins). Non-limiting examples of such process development stages that can employ methods of the present disclosure include cell selection, clonal selection, media optimization, culture conditions, process conditions, and/or purification procedure. Those of ordinary skill in the art will be aware of other process development stages.

The methods of the present disclosure can also be utilized to monitor the extent and/or type of protein conformation or aggregation occurring in a particular cell culture, thereby allowing adjustment or possibly termination of the culture in order, for example, to achieve a particular desired protein conformation or aggregation state or to avoid development of a particular undesired protein conformation or aggregation state.

The methods of the present disclosure can also be utilized to assess the properties of cells or cell lines that are being considered for production of a particular desired protein (for example, even before the cells or cell lines have been engineered to produce the protein, or to produce the protein at a commercially relevant level).

In some embodiments of the disclosure, a desired protein conformation for a particular target protein (e.g., a glycoprotein) is known, and the technology described herein allows monitoring of culture samples to assess progress of the production along a route known to produce the desired protein conformation. For example, where the target protein is a therapeutic glycoprotein, for example having undergone regulatory review in one or more countries, it will often be desirable to monitor cultures to assess the likelihood that they will generate a product with a protein conformation as close to the established conformation of the pharmaceutical product as possible, whether or not it is being produced by exactly the same route. As used herein, "close" refers to a protein conformation having at least a 75%, 80%, 85%, 90%, 95%, 98% or 99% correlation to the established protein confirmation of the pharmaceutical product. In such embodiments, samples of the production culture are typically taken at multiple time points and are compared with an established standard or with a control culture in order to assess relative conformations.

Whether or not monitoring production of a particular target protein for quality control purposes, the methods of the present disclosure may be utilized, for example, to monitor protein conformation and/or aggregation at particular stages of development, or under particular growth conditions.

In some particular embodiments of the present disclosure methods described herein can be used to characterize and/or control or compare the quality of therapeutic products. To give but one example, the present methodologies can be used to assess protein conformation in cells producing a therapeutic protein product. Particularly given that protein conformation can often affect the activity, bioavailability, or other characteristics of a therapeutic protein product, methods for assessing protein conformation during production of such a therapeutic protein product are particularly desirable. Among other things, the methods can facilitate real time analysis of protein conformation in production systems for therapeutic proteins.

It will be appreciated that the methods described herein are not limited to any particular protein or protein type. Representative therapeutic glycoprotein products whose production and/or quality can be monitored include, for example, any of a variety of hematologic agents (including, for instance, erythropoietins, blood-clotting factors, etc.), inter ferons, colony stimulating factors, antibodies, enzymes, and hormones.

Representative commercially available glycoprotein products include, for example:

| Protein Product | Reference Drug |
|---|---|
| interferon gamma-1b | Actimmune ® |
| alteplase; tissue plasminogen activator | Activase ®/Cathflo ® |
| Recombinant antihemophilic factor | Advate |
| human albumin | Albutein ® |
| laronidase | Aldurazyme ® |
| interferon alfa-N3, human leukocyte derived | Alferon N ® |
| human antihemophilic factor | Alphanate ® |
| virus-filtered human coagulation factor IX | AlphaNine ® SD |
| Alefacept; recombinant, dimeric fusion protein LFA3-Ig | Amevive ® |
| bivalirudin | Angiomax ® |
| darbepoetin alfa | Aranesp ™ |
| bevacizumab | Avastin ™ |
| interferon beta-1a; recombinant | Avonex ® |
| coagulation factor IX | BeneFix ™ |
| Interferon beta-1b | Betaseron ® |
| Tositumomab | Bexxar ® |
| antihemophilic factor | Bioclate ™ |
| human growth hormone | BioTropin ™ |
| botulinum toxin type A | Botox ® |
| alemtuzumab | Campath ® |
| acritumomab; technetium-99 labeled | CEA-Scan ® |
| alglucerase; modified form of beta-glucocerebrosidase | Ceredase ® |
| imiglucerase; recombinant form of beta-glucocerebrosidase | Cerezyme ® |
| crotalidae polyvalent immune Fab, ovine | CroFab ™ |
| digoxin immune Fab, ovine | DigiFab ™ |
| rasburicase | Elitek ® |
| etanercept | Enbrel ® |
| epoietin alfa | Epogen ® |
| cetuximab | Erbitux ™ |
| algasidase beta | Fabrazyme ® |
| urofollitropin | Fertinex ™ |
| follitropin beta | Follistim ™ |
| teriparatide | Forteo ® |
| human somatropin | GenoTropin ® |
| glucagon | GlucaGen ® |
| follitropin alfa | Gonal-F ® |
| antihemophilic factor | Helixate ® |
| Antihemophilic Factor; Factor XIII | Hemofil ® |
| insulin | Humalog ® |
| antihemophilic factor/von Willebrand factor complex-human | Humate-P ® |
| somatotropin | Humatrope ® |
| adalimumab | HUMIRA ™ |
| human insulin | Humulin ® |
| recombinant human hyaluronidase | Hylenex ™ |
| interferon alfacon-1 | Infergen ® |
| Eptifibatide | Integrilin ™ |
| alpha-interferon | Intron A ® |
| palifermin | Kepivance |
| anakinra | Kineret ™ |
| antihemophilic factor | Kogenate ® FS |
| insulin glargine | Lantus ® |
| granulocyte macrophage colony-stimulating factor | Leukine ®/Leukine ® Liquid |
| lutropin alfa, for injection | Luveris |
| OspA lipoprotein | LYMErix ™ |
| ranibizumab | Lucentis ® |
| gemtuzumab ozogamicin | Mylotarg ™ |
| galsulfase | Naglazyme ™ |
| nesiritide | Natrecor ® |
| pegfilgrastim | Neulasta ™ |
| oprelvekin | Neumega ® |
| filgrastim | Neupogen ® |
| fanolesomab | NeutroSpec ™ (formerly LeuTech ®) |
| somatropin [rDNA] | Norditropin ®/Norditropin Nordiflex ® |
| insulin; zinc suspension; | Novolin L ® |
| insulin; isophane suspension | Novolin N ® |
| insulin, regular; | Novolin R ® |
| insulin | Novolin ® |
| coagulation factor VIIa | NovoSeven ® |
| somatropin | Nutropin ® |
| immunoglobulin intravenous | Octagam ® |
| PEG-L-asparaginase | Oncaspar ® |

-continued

| Protein Product | Reference Drug |
|---|---|
| abatacept, fully human soluable fusion protein | Orencia ™ |
| muromomab-CD3 | Orthoclone OKT3 ® |
| human chorionic gonadotropin | Ovidrel ® |
| peginterferon alfa-2a | Pegasys ® |
| pegylated version of interferon alfa-2b | PEG-Intron ™ |
| Abarelix (injectable suspension); gonadotropin-releasing hormone antagonist | Plenaxis ™ |
| epoietin alfa | Procrit ® |
| aldesleukin | Proleukin, IL-2 ® |
| somatrem | Protropin ® |
| dornase alfa | Pulmozyme ® |
| Efalizumab; selective, reversible T-cell blocker | Raptiva ™ |
| combination of ribavirin and alpha interferon | Rebetron ™ |
| Interferon beta 1a | Rebif ® |
| antihemophilic factor | Recombinate ® |
| rAHF/ntihemophilic factor | ReFacto ® |
| lepirudin | Refludan ® |
| infliximab | Remicade ® |
| abciximab | ReoPro ™ |
| reteplase | Retavase ™ |
| rituximab | Rituxan ™ |
| interferon alfa-2a | Roferon-A ® |
| somatropin | Saizen ® |
| synthetic porcine secretin | SecreFlo ™ |
| basiliximab | Simulect ® |
| eculizumab | Soliris ® |
| pegvisomant | Somavert ® |
| Palivizumab; recombinantly produced, humanized mAb | Synagis ™ |
| thyrotropin alfa | Thyrogen ® |
| tenecteplase | TNKase ™ |
| natalizumab | Tysabri ® |
| human immune globulin intravenous 5% and 10% solutions | Venoglobulin-S ® |
| interferon alfa-n1, lymphoblastoid | Wellferon ® |
| drotrecogin alfa | Xigris ™ |
| Omalizumab; recombinant DNA-derived humanized monoclonal antibody targeting immunoglobulin-E | Xolair ® |
| daclizumab | Zenapax ® |
| ibritumomab tiuxetan | Zevalin ™ |
| Somatotropin | Zorbtive ™ (Serostim ®) |

In some embodiments, the disclosure provides methods in which proteins from different sources or samples are compared with one another. In certain embodiments, the disclosure provides methods used to monitor the protein conformations occurring in different cell cultures. In some such examples, multiple samples from the same source are obtained over time, so that relevant changes are monitored. In some embodiments, one of the samples is a historical sample or a record of a historical sample. In some embodiments, one of the samples is a reference sample. For example, in certain embodiments, the disclosure provides methods used to monitor protein conformations occurring in different cell cultures.

In some embodiments, protein preparations from different cell culture samples prepared under conditions that differ in one or more parameters (e.g., cell type, culture type [e.g., continuous feed versus batch feed, etc.], culture conditions [e.g., type of media, presence or concentration of particular component of particular medium(a), osmolarity, pH, temperature, timing or degree of shift in one or more components such as osmolarity, pH, temperature, etc.], culture time, isolation steps, etc.) but are otherwise identical, are compared, so that effects of the selected parameter(s) on protein conformation are determined. In certain embodiments, proteins from different cell culture samples prepared under conditions that differ in a single selected parameter are compared so that the effect of the single selected parameter on protein conformation is determined. Among other applications, therefore, use of techniques as described herein may facilitate determination of the effects of particular parameters on protein folding in cells.

In some embodiments, protein preparations from different batches of a protein of interest (e.g., a therapeutic glycoprotein), whether prepared by the same method or by different methods, and whether prepared simultaneously or separately, are compared. In such embodiments, the present disclosure facilitates quality control of protein preparation.

Alternatively or additionally, some such embodiments facilitate monitoring of progress of a particular culture producing a protein of interest (e.g., when samples are removed from the culture at different time points and are analyzed and compared to one another). In any of these embodiments, features of the protein conformation can be recorded, for example in a quality control record. As indicated above, in some embodiments, a comparison is with a historical record of a prior or standard batch and/or with a reference sample of the same protein.

In certain embodiments, the methods may be utilized in studies to modify the properties of a cell, for example to establish a cell line and/or culture conditions with one or more desirable protein folding characteristics. Such a cell line and/or culture conditions can then be utilized, if desired, for production of a particular target protein (e.g., a therapeutic glycoprotein) for which such folding properties are expected to be beneficial.

In certain embodiments, techniques of the present disclosure are applied to cell-surface proteins. In certain embodiments, techniques of the present disclosure are applied to proteins that are secreted from cells. In certain embodiments, techniques of the present disclosure are applied to glycoproteins. In certain embodiments, techniques of the present disclosure are applied to proteins that are not glycosylated.

According to the present disclosure, techniques described herein can be used to detect desirable or undesirable proteins, for example to detect or quantify the presence of one or more improperly folded or aggregated proteins in a product, or to detect or quantify the presence of one or more active or desired species.

In some embodiments, techniques described herein may be combined with one or more other technologies for the detection, analysis, and or isolation of proteins. In particular, it will be appreciated that differences detected by circular dichroism (CD), differential scanning calorimetery (DSC), dynamic light scattering (DLS), fluorescence emission spectroscopy, derivative UV spectroscopy, or infrared spectroscopy (IR), etc. may be used in addition to differences detected by NOESY NMR in order to compare the conformations of proteins in two or more protein preparations.

The methods will be more specifically illustrated by the following examples. However, it should be understood that the methods are not limited by these examples in any manner.

EXAMPLES

A 2D $^1$H-$^1$H NOESY NMR spectrum of the protein CSP-sg4 (Picone et al., *Eur. J. Biochem.* 268:4794-4801, 2001) was obtained at 1.2 mM protein concentration, in 50 mM sodium phosphate buffer, pH 6.8, at 300 K, with a 100 ms mixing time. FIG. 1 shows the NH—NH correlation region of this spectrum (about 6 to 10 ppm). As shown, this spectral region is well resolved since the amide NH chemical shift is highly sensitive to chemical environment and therefore well distributed in both dimensions. In addition, this region is well separated from the strong H$_2$O resonance (~4.8 ppm). Further, since each amino acid includes a single amide, the correlations in this region are, by definition, inter residue correlations. The intensities and chemical shifts of the resolved cross-peaks in this region may be used to compare the conformations of different protein preparations of CSP-sg4.

Equivalents

All literature and similar material cited in this application, including, but not limited to, patents, patent applications, articles, books, treatises, and web pages, regardless of the format of such literature and similar materials, are expressly incorporated by reference in their entirety. In the event that one or more of the incorporated literature and similar materials differs from or contradicts this application, including but not limited to defined terms, term usage, described techniques, or the like, this application controls. The section headings used herein are for organizational purposes only and are not to be construed as limiting the subject matter described in any way. While the methods have been described in conjunction with various embodiments and examples, it is not intended that the methods be limited to such embodiments or examples. On the contrary, the methods encompass various alternatives, modifications, and equivalents, as will be appreciated by those of skill in the art.

While the methods has been particularly shown and described with reference to specific illustrative embodiments, it should be understood that various changes in form and detail may be made without departing from the spirit and scope of the present disclosure. Therefore, all embodiments that come within the scope and spirit of the methods, and equivalents thereto, are intended to be claimed. The claims, descriptions and diagrams of the methods, systems, and assays of the present disclosure should not be read as limited to the described order of elements unless stated to that effect.

We claim:

1. A method of measuring differences in relative conformations of a recombinant glycoprotein provided in different preparations, comprising steps of:
   generating a first 2D NOESY NMR spectrum of a first preparation of a recombinant glycoprotein using an NMR spectrometer, wherein the recombinant glycoprotein has been recombinantly expressed in a mammalian cell;
   generating a second 2D NOESY NMR spectrum, comparable to the first spectrum, of a second preparation of the same recombinant glycoprotein using an NMR spectrometer, wherein the recombinant gycoprotein has been recombinantly expressed in a mammalian cell; and
   measuring differences in conformation of the recombinant glycoprotein in the first and second glycoprotein preparations by comparing one or more cross-peaks in the first 2D NOESY NMR spectrum with one or more corresponding cross-peaks in the second 2D NOESY NMR spectrum.

2. The method of claim 1, wherein the step of measuring comprises:
   comparing chemical shifts of one or more cross-peaks in the first 2D NOESY NMR spectrum with chemical shifts of one or more corresponding cross-peaks in the second 2D NOESY NMR spectrum.

3. The method of claim 1, wherein the step of measuring comprises:
   comparing intensities of one or more cross-peaks in the first 2D NOESY NMR spectrum with intensities of one or more corresponding cross-peaks in the second 2D NOESY NMR spectrum.

4. The method of claim 1, wherein the second glycoprotein preparation is a therapeutic glycoprotein product.

5. The method of claim 1, wherein the first and second glycoprotein preparations were prepared by the same method.

6. The method of claim 1, wherein the first and second glycoprotein preparations were prepared by different methods.

7. The method of claim 1, wherein the one or more cross-peaks are the result of correlations between amide NH nuclei.

8. The method of claim 1, wherein the one or more cross-peaks are the result of correlations between amide NH nuclei and CH$_3$ methyl nuclei.

9. The method of claim 1, wherein the one or more cross-peaks are the result of correlations between CH$_3$ methyl nuclei.

10. The method of claim 1, wherein the one or more cross-peaks are the result of correlations between amide NH nuclei and indole NH nuclei.

11. The method of claim 1, wherein the one or more cross-peaks are the result of correlations between CH$_3$ methyl nuclei and indole NH nuclei.

12. The method of claim 1, wherein the one or more cross-peaks are the result of correlations between amide NH nuclei and H-α nuclei.

13. The method of claim 1, wherein the one or more cross-peaks are the result of correlations between amide NH nuclei and glycosidic nuclei.

14. The method of claim 1 further comprising a step of: assigning the one or more cross-peaks.

15. A method of producing a recombinant glycoprotein, comprising steps of:
providing a first preparation of a recombinant glycoprotein from a mammalian cell culture expressing the recombinant glycoprotein;
providing a second preparation of the same recombinant glycoprotein from a mammalian cell culture expressing the recombinant glycoprotein;
obtaining a first 2D NOESY NMR spectrum of the first preparation;
obtaining a second 2D NOESY NMR spectrum, comparable to the first spectrum, of the second preparation;
determining relative conformations of the recombinant glycoprotein in the first and second glycoprotein preparations by comparing one or more cross-peaks in the first 2D NOESY NMR spectrum with one or more corresponding cross-peaks in the second 2D NOESY NMR spectrum; and
producing the recombinant glycoprotein in the mammalian cell culture if the relative conformations of the recombinant glycoprotein in the first and second glycoprotein preparations are at least 75% similar.

16. The method of claim 15, wherein the step of determining comprises:
comparing chemical shifts of one or more cross-peaks in the first 2D NOESY NMR spectrum with chemical shifts of one or more corresponding cross-peaks in the second 2D NOESY NMR spectrum.

17. The method of claim 15, wherein the step of determining comprises:
comparing intensities of one or more cross-peaks in the first 2D NOESY NMR spectrum with intensities of one or more corresponding cross-peaks in the second 2D NOESY NMR spectrum.

18. The method of claim 15, wherein the first glycoprotein preparation is a therapeutic glycoprotein product.

19. The method of claim 15, wherein the first and second glycoprotein preparations were prepared by the same method.

20. The method of claim 15, wherein the first and second glycoprotein preparations were prepared by different methods.

21. The method of claim 15, wherein the one or more cross-peaks are the result of correlations between amide NH nuclei.

22. The method of claim 15, wherein the one or more cross-peaks are the result of correlations between amide NH nuclei and $CH_3$ methyl nuclei.

23. The method of claim 15, wherein the one or more cross-peaks are the result of correlations between $CH_3$ methyl nuclei.

24. The method of claim 15, wherein the one or more cross-peaks are the result of correlations between amide NH nuclei and indole NH nuclei.

25. The method of claim 15, wherein the one or more cross-peaks are the result of correlations between $CH_3$ methyl nuclei and indole NH nuclei.

26. The method of claim 15, wherein the one or more cross-peaks are the result of correlations between amide NH nuclei and H-α nuclei.

27. The method of claim 15, wherein the one or more cross-peaks are the result of correlations between amide NH nuclei and glycosidic nuclei.

28. The method of claim 15 further comprising a step of assigning the one or more cross-peaks.

29. The method of claim 4, wherein the therapeutic glycoprotein product is a therapeutic antibody.

30. The method of claim 4, wherein the therapeutic glycoprotein product is alemtuzumab, etanercept, adalimumab, abatacept, infliximab, bevacizumab, rituximab, natalizumab, or cetuximab.

31. The method of claim 18, wherein the therapeutic glycoprotein product is a therapeutic antibody.

32. The method of claim 18, wherein the therapeutic glycoprotein product is alemtuzumab, etanercept, adalimumab, abatacept, infliximab, bevacizumab, rituximab, natalizumab, or cetuximab.

33. The method of claim 1, wherein the first preparation is a solution and the second preparation is a solution, and wherein the solution of the first preparation and the solution of the second preparation are substantially the same.

34. The method of claim 15, wherein the first preparation is a solution and the second preparation is a solution, and wherein the solution of the first preparation and the solution of the second preparation are substantially the same.

* * * * *